(12) United States Patent
Seppä et al.

(10) Patent No.: US 9,649,070 B2
(45) Date of Patent: May 16, 2017

(54) METHOD FOR DECOMPOSITION OF A COMPOSITE SIGNAL CONSISTING OF OSCILLATORY WAVEFORMS AND A MODULATING SIGNAL

(75) Inventors: Ville-Pekka Seppä, Tampere (FI); Jari Viik, Tampere (FI); Jari Hyttinen, Tampere (FI)

(73) Assignee: TIDE MEDICAL OY, Tampere (FI)

( * ) Notice: Subject to any disclaimer, the term of this patent is extended or adjusted under 35 U.S.C. 154(b) by 947 days.

(21) Appl. No.: 13/983,252

(22) PCT Filed: Feb. 2, 2012

(86) PCT No.: PCT/FI2012/050099
§ 371 (c)(1),
(2), (4) Date: Oct. 3, 2013

(87) PCT Pub. No.: WO2012/104490
PCT Pub. Date: Aug. 9, 2012

(65) Prior Publication Data
US 2014/0024958 A1    Jan. 23, 2014

(30) Foreign Application Priority Data
Feb. 3, 2011    (FI) .................................... 20115110

(51) Int. Cl.
*A61B 5/00*        (2006.01)
*A61B 5/0452*    (2006.01)
(Continued)

(52) U.S. Cl.
CPC .......... *A61B 5/7207* (2013.01); *A61B 5/0452* (2013.01); *A61B 5/0535* (2013.01);
(Continued)

(58) Field of Classification Search
CPC ... A61B 5/0402; A61B 5/0452–5/0472; A61B 5/05; A61B 5/053–5/0535;
(Continued)

(56) References Cited

U.S. PATENT DOCUMENTS 4,781,201 A      11/1988   Wright et al.
6,132,381 A *  10/2000   Forbes ................. A61B 5/0452
                                                                                600/483

(Continued)

FOREIGN PATENT DOCUMENTS

EP      0 434 856 A1      7/1991
EP      0 647 426 A2      4/1995

OTHER PUBLICATIONS

International Search Report for PCT/FI2012/050099 issued Jun. 11, 2012, 4 pages.

(Continued)

*Primary Examiner* — Jacqueline Cheng
*Assistant Examiner* — Jairo Portillo
(74) *Attorney, Agent, or Firm* — Foley & Lardner LLP

(57) ABSTRACT

Various embodiments relate to a method, apparatus, system, and a computer program product for suppressing an oscillatory signal Sosc. In the method a composite signal S comprising said Sosc and a modulating signal Smod are provided and the S is high pass filtered to produce estimates of the Sosc and the Smod, wherein the estimate of the Sosc comprises first oscillations during a first state of the modulating signal and second oscillations during a second state of the modulating signal. A first bin associated with said first state and a second bin associated with said second state are defined and assigned for said first oscillation and the second bin for said second oscillation according to a state defined from the estimate of the Smod. A first average waveform for said first oscillations and a second average waveform for (Continued)

said second oscillations are formed and used to suppress the Sosc signal from the composite signal S.

18 Claims, 6 Drawing Sheets

(51) Int. Cl.
    *A61B 5/085*     (2006.01)
    *A61B 5/053*     (2006.01)
    *A61B 5/08*     (2006.01)

(52) U.S. Cl.
    CPC ............ *A61B 5/085* (2013.01); *A61B 5/0809* (2013.01); *A61B 5/725* (2013.01)

(58) Field of Classification Search
    CPC .................. A61B 5/0809; A61B 5/085; A61B 5/72–5/7207; A61B 5/7214; A61B 5/7235; A61B 5/725
    See application file for complete search history.

(56) References Cited

U.S. PATENT DOCUMENTS

| | | | |
|---|---|---|---|
| 2004/0006279 A1* | 1/2004 | Arad (Abboud) | ... A61B 5/0536 600/506 |
| 2010/0076329 A1* | 3/2010 | Toth | ................... A61B 5/04012 600/509 |

OTHER PUBLICATIONS

Du X.T. et al., Study on the New Method of Heart Disturbance Filtering on Measurement of Impedance Pneumograph, Journal of Physics: Conference Series 48 (2006) 1147-1151.

Seppä, Ville-Pekka et al., Assessment of Pulmonary Flow Using Impedance Pneumography, IEEE Transactions on Biomedical Engineering, vol. 57, No. 9, Sep. 2010, 2277-2285.

Schuessler, T. et al., An Adaptive Filter to Reduce Cardiogenic Oscillations on Esophageal Pressure Signals, Annals of Biomedical Engineering. vol. 26, pp. 260-267, 1998.

* cited by examiner

METHOD FOR DECOMPOSITION OF A COMPOSITE SIGNAL CONSISTING OF OSCILLATORY WAVEFORMS AND A MODULATING SIGNAL

CROSS-REFERENCE TO RELATED APPLICATIONS

The present application is a U.S. National Stage Application of International Application No. PCT/FI2012/050099, filed on Feb. 2, 2012, which claims priority to Finland Patent Application No. 20115110, filed Feb. 3, 2011. The contents of both applications are hereby incorporated herein by reference in their entirety.

FIELD OF THE INVENTION

The present invention relates to a method, a system, an apparatus and a computer program product for suppressing an oscillatory signal from a composite signal comprising an oscillatory signal and a signal that is modulating the oscillatory signal.

BACKGROUND OF THE INVENTION

Physiological time-series signals measured from the human body or other organism often constitute of two summed signals, where one is of oscillatory transient type, an oscillatory signal, and the other one a modulating signal. The modulating signal is continuous periodic signal that has lower frequency than the oscillatory signal. The oscillatory signal occurs at certain time intervals due to a triggering event. The trigger can be internal, like the heart sinus node activation starting a heart contraction, or external, like a flash of light triggering an evoked potential in the brain. Oftentimes the measured signals caused by these oscillatory events change shape due to some external factor. For instance, the shape of the electrocardiographic signals recorded for each heart contraction change shape with respiration. The oscillations and the modulating signal can also be summed together as is the case in the thoracic cardiac and respiratory impedance signals.

In impedance pneumography, the transthoracic electrical impedance varies over time due to the cardiac function and the respiration. Cardiogenic impedance signal Zc, that is cardiogenic part of impedance signal Z, originates from the movement of blood volumes in the thorax, and the respiratory impedance signal Zr, that is respiratory part of impedance signal Z, is directly proportional to the lung volume. These measurable signals can be exploited to analyze cardiac function, as in impedance cardiography (ICG), or lung function, as in impedance pneumography (IP). For reliable analysis of the pulmonary variables of interest should the cardiogenic impedance signal Zc, an additive noise signal, to be suppressed, because presence of the cardiogenic oscillations (CGO) hinders the accurate segmentation of the impedance signal into respiratory cycles and finding of the points of interest, like time of peak expiratory flow. Preserving the harmonic components of the respiration signal is important in the emerging IP applications, like ambulatory long-term lung function assessment, where tidal breathing parameters more complex than respiration rate or tidal volume may be extracted from the impedance signal Z.

The frequency spectra of the cardiogenic impedance signal Zc and the respiratory impedance signal Zr have their corresponding main power components at the frequencies of heart rate (HR) and respiration rate (RR), respectively. The main cardiac component is typically at a frequency at least two times higher than that of the respiration. However, the harmonic frequencies of the cardiogenic impedance signal Zc contain power that reach the HR frequency causing the power spectrum of the two signals to overlap.

Thus, if CGO are removed the with a normal linear low pass filter with cut-off frequency slightly below the HR, some information of the respiratory impedance signal may also be removed. This problem may be pronounced in subjects with high RR to HR ratio.

European patent EP434856B1, "Method of deriving a respiration signal and/or a cardiac artefact signal from a physiological signal," discloses a method of deriving a respiration signal and/or a cardiac artefact signal from a physiological signal having at least a respiration signal component and a cardiac artefact signal component, in particular from an impedance pneumography signal. However, this method does not recognize the interaction between the cardiac oscillation signal and the lung volume. On the contrary, it is stated that the cardiac artifact signal has a waveform which in terms of time remains substantially the same from one heartbeat to another heartbeat.

There is, therefore, a need for a solution that attenuates the cardiogenic oscillations in impedance pneumography signal by taking into account the modulating effect that the changing lung volume has on the cardiogenic oscillation waveform.

SUMMARY OF THE INVENTION

Now there has been invented an improved method and technical equipment implementing the method, by which the above problems are alleviated. Various aspects of the invention include a method, an apparatus, a system and a computer readable medium comprising a computer program stored therein, which are characterized by what is stated in the independent claims. Various embodiments of the invention are disclosed in the dependent claims.

According to a first aspect, there is provided a method for suppressing an oscillatory signal Sosc by providing a composite signal S comprising said oscillatory signal Sosc and a modulating signal Smod; high pass filtering the composite signal S with a high pass filter to produce an estimate of the oscillatory signal Ŝosc and an estimate of the modulating signal Ŝmod, wherein the estimate of the oscillatory signal Ŝosc comprises first oscillations during a first state of the modulating signal Smod and second oscillations during a second state of the modulating signal Smod; defining a first bin associated with said first state and a second bin associated with said second state; assigning the first bin for said first oscillation according to a state defined from the estimate of the modulating signal Ŝmod and the second bin for said second oscillation according to a state defined from the estimate of the modulating signal Ŝmod; forming a first average waveform for said first oscillations in said first bin and a second average waveform for said second oscillations in said second bin; and using said first and second average waveforms for suppressing said oscillatory signal Sosc from said composite signal S in the respective states of said first and second average waveforms. In the method the composite signal S is a transthoracic electrical impedance signal Z, the modulating signal Smod is a respiratory part of the transthoracic electrical impedance signal Zr and Sosc is a cardiogenic part of the transthoracic electrical impedance signal Zc.

In other words, an oscillatory signal Sosc can be suppressed from a composite signal S comprising the oscillatory signal Sosc and a modulating signal Smod without removing parts of the modulating signal Smod. The composite signal S is high pass filtered to produce estimates of oscillatory signal Sosc and the modulating signal Ŝmod. The estimate of the oscillatory signal Ŝosc comprises at least first oscillations during a first state of the modulating signal Smod and second oscillations during a second state of the modulating signal Smod. A first bin associated with said first state and a second bin associated with said second state are defined and the first bin for said first oscillation according to a state defined from the estimate of the modulating signal Ŝmod and the second bin for said second oscillation according to a state defined from the estimate of the modulating signal Ŝmod are assigned. A first average waveform for said first oscillations in said first bin and a second average waveform for said second oscillations in said second bin are formed. And these first and second average waveforms are subtracted from the composite signal S in the respective states of said first and second average waveforms to form the modulating signal Smod. The method may be applied, for example, for suppressing the cardiogenic oscillations in an impedance pneumography signal, wherein the cardiogenic oscillations and the impedance respiratory signal form a transthoracic impedance signal.

According to a second aspect, there is provided a system comprising at least a measuring unit and a processing unit that comprises at least a memory and a computer program product stored on a memory comprising a computer program code configured to perform the method for suppressing an oscillatory signal Sosc by providing a composite signal S comprising said oscillatory signal Sosc and a modulating signal Smod; high pass filtering the composite signal S with a high pass filter to produce an estimate of the oscillatory signal Ŝosc and an estimate of the modulating signal Ŝmod, wherein the estimate of the oscillatory signal Ŝosc comprises first oscillations during a first state of the modulating signal Smod and second oscillations during a second state of the modulating signal Smod; defining a first bin associated with said first state and a second bin associated with said second state; assigning the first bin for said first oscillation according to a state defined from the estimate of the modulating signal Ŝmod and the second bin for said second oscillation according to a state defined from the estimate of the modulating signal Ŝmod; forming a first average waveform for said first oscillations in said first bin and a second average waveform for said second oscillations in said second bin; and using said first and second average waveforms for suppressing said oscillatory signal Sosc from said composite signal S in the respective states of said first and second average waveforms.

According to a third aspect, there is provided an apparatus comprising a memory and a computer program product stored on a memory comprising a computer program code configured to perform the method for suppressing an oscillatory signal Sosc by providing a composite signal S comprising said oscillatory signal Sosc and a modulating signal Smod; high pass filtering the composite signal S with a high pass filter to produce an estimate of the oscillatory signal Ŝosc and an estimate of the modulating signal Ŝmod, wherein the estimate of the oscillatory signal Ŝosc comprises first oscillations during a first state of the modulating signal Smod and second oscillations during a second state of the modulating signal Smod; defining a first bin associated with said first state and a second bin associated with said second state; assigning the first bin for said first oscillation according to a state defined from the estimate of the modulating signal Ŝmod and the second bin for said second oscillation according to a state defined from the estimate of the modulating signal Ŝmod; forming a first average waveform for said first oscillations in said first bin and a second average waveform for said second oscillations in said second bin; and using said first and second average waveforms for suppressing said oscillatory signal Sosc from said composite signal S in the respective states of said first and second average waveforms.

According to a fourth aspect, there is provided a computer program product stored on a storage medium comprising a computer program code configured to, with at least one processor, cause an apparatus to provide a composite signal S comprising said oscillatory signal Sosc and a modulating signal Smod; high pass filter the composite signal S with a high pass filter to produce an estimate of the oscillatory signal Ŝosc and an estimate of the modulating signal Ŝmod, wherein the estimate of the oscillatory signal Ŝosc comprises first oscillations during a first state of the modulating signal Ŝmod and second oscillations during a second state of the modulating signal Smod; define a first bin associated with said first state and a second bin associated with said second state; assign the first bin for said first oscillation according to a state defined from the estimate of the modulating signal Ŝmod and the second bin for said second oscillation according to a state defined from the estimate of the modulating signal Ŝmod; form a first average waveform for said first oscillations in said first bin and a second average waveform for said second oscillations in said second bin; and use said first and second average waveforms for suppressing said oscillatory signal Sosc from said composite signal S in the respective states of said first and second average waveforms.

DESCRIPTION OF THE DRAWINGS

In the following, various embodiments of the invention will be described in more detail with reference to the appended drawings, in which.

DETAILED DESCRIPTION OF THE EMBODIMENTS

The method of present invention may be used to decompose and suppress oscillations in various applications like respiratory inductive plethysmography, pulse plethysmography, esophageal pressure signals, pulmonary airflow signal or any other noninvasively or invasively acquired physiological signals. The transient oscillatory signal Sosc maybe modulated by a lower frequency signal Smod. According to one exemplary embodiment the oscillatory signal does not need to involve heart nor does the modulating signal need to involve respiration. In addition, it is not required for the signals to be of physiological origin. A composite signal S comprises a transient oscillatory signal Sosc and the modulating signal Smod:

$$S = Smod + Sosc,$$

wherein Smod is modulating Sosc through an unknown modulation function.

In the following, embodiments of the invention will be described in the context of figures. It is to be noted, that the invention is not limited to these embodiments.

Figure 1:
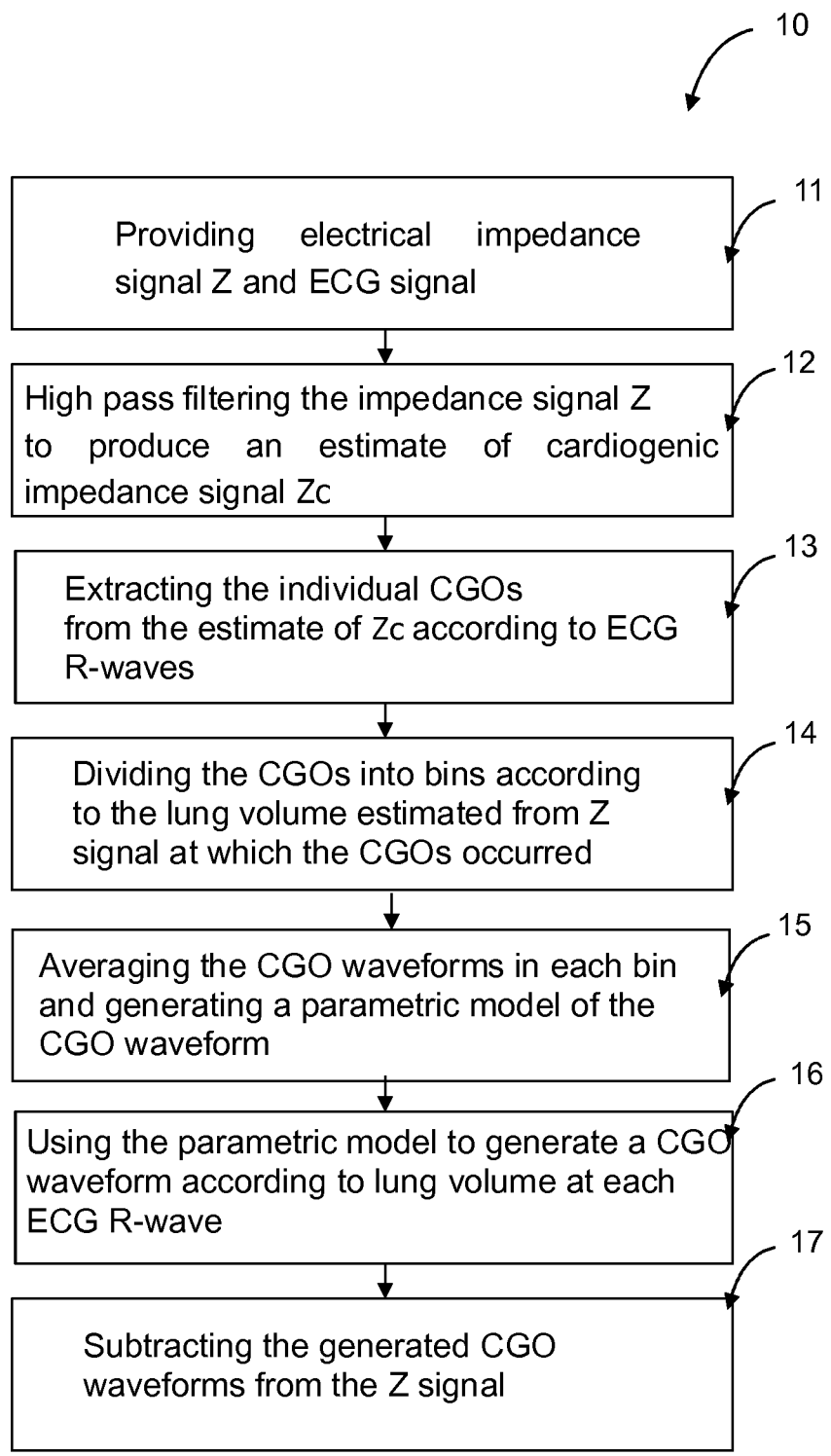
FIG. 1 shows a flowchart illustrating the steps employed in cancelling a cardiogenic impedance signal Zc from the impedance signal Z without altering the respiratory part Zr of the impedance signal Z, by forming a static parametric model of the cardiogenic oscillation, according to one embodiment of the present invention.

FIG. 1 shows a flow chart of a method 10 for cancelling Zc, that is a cardiogenic part of a transthoracic electrical impedance signal Z, from the transthoracic electrical impedance signal Z without altering the respiratory part Zr of the impedance signal Z by forming a static parametric model of the cardiogenic oscillation, according to one embodiment of the present invention. The method 10 is especially suitable for shorter measurement periods, for example, a 10 minutes or 50 respiratory cycles long measurement, during which the posture and physiological state of a measuring subject remains substantially constant and the CGO waveform will not change substantially due postural and/or physiological changes. Thus, it is possible to obtain a reliable Zr signal by using a parametric model of the CGO that is modulated by lung volume or other respiratory parameter in filtering of the Z signal. In this embodiment of the invention, the parametric model remains time-wise static once it is defined. It is not recursively adapted over time as in a method disclosed in context with FIG. 2. A transthoracic impedance signal Z is one example of the said composite signal S, where Zc corresponds to Sosc and Zr corresponds to Smod.

The method 10 proceeds from the beginning of the measurement signals Z and electrocardiogram (ECG) towards the end of the signals Z and ECG in time by processing Z signal segments defined in time by two consecutive ECG signal R-waves. The trigger signal may also be any other signal than ECG, like plethysmographic or pressure signal, that can be used to determine heart contraction timings or the segments can even be defined without any external trigger signal finding the contraction timings from the impedance signal itself.

At stage 11, the impedance signal Z and ECG are provided for a signal processing apparatus. The apparatus may be, for example, a special equipment for measuring and analyzing impedance data, a mobile terminal, a laptop computer, personal computer (PC) or any other data processing device that may comprise means for receiving or recording impedance and electrocardiogram (ECG) signals, means for signal processing and a memory. The memory may be any means for storing, for example, an internal memory of the apparatus. The Z and ECG signals maybe acquired from separate devices or from the same device using separate electrodes or the same electrodes for both.

At stage 12, an estimate of Zc, that is $\hat{Z}c$, may be obtained by high pass filtering the original impedance signal Z with a high pass filter with a predetermined cut-off frequency 0.6 times of heart rate (HR). The cut off frequency may also be determined to be, for example, 0.5-0.9 times HR. The $\hat{Z}c$ consists mostly of cardiogenic components, but it also contains some traces of the respiratory signal Zr as the frequency spectra of the two signals overlap. Additionally, an estimate of Zr, that is $\hat{Z}r$, is produced as $\hat{Z}r = Z - \hat{Z}c$.

At stage 13, a single cardiogenic oscillation (CGO) as a segment of $\hat{Z}c$ between two consecutive ECG R-wave is extracted. The beginning and the end of the CGO signal are made zero values, in case they are not already zero. To make the beginning of the CGO signal zero, the value of the first sample may be subtracted from all samples of the CGO. For the end, a line between the first and the last sample may be subtracted from all samples of the CGO, or the end of the CGO sample may be convoluted with a decaying sample train ranging between 1 and 0. The amount of samples may be fixed by re-sampling the segment of $\hat{Z}c$ into a chosen amount of samples.

At stage 14, the CGOs are put into a number of bins according to the relative lung volume, respiratory cycle phase or similar periodic parameter derived from the $\hat{Z}r$ signal that is modulating the CGO waveform shape. The value of the chosen parameter defined from the Z signal can be defined in the beginning, middle or end, or any other location during the particular CGO. The value may also be an average of multiple values during the CGO. This obtained value is then used to choose an appropriate bin for the each CGO. The number of the bins and their limits in the value range can be freely defined. For example, four bins with limits of 0-25%, 26-50%, 51-75% and 76-100% of the $\hat{Z}r$ values (relative lung volume) encountered during a particular respiratory cycle.

At stage 15, once all the CGOs have been assigned into bins, a single representative CGO waveform is obtained for each bin by averaging the individual measured CGOs in each bin. The averaging may be achieved by mean, weighted mean, median or any other averaging function. The averaging suppresses the traces of the respiratory signal left after the high pass filtering because the traces of the respiratory signal are stochastic with respect to the CGO events. Then the averaged waveforms are used to construct a parametric model for the CGO waveform. The model outputs a representative CGO waveform for any particular value of the parameter that was used to divide the CGOs into bins, for example the relative lung volume. This model may be achieved, for example, by fitting a spline to each of the averaged CGO waveforms, obtaining a number of knot points in the waveform (disclosed in FIG. 5). Each of these knot points may then be assigned a piece-wise continuous function or any other function that takes the bin parameter as argument, for example, the relative lung volume, i.e. parametrizing the waveform. Thus, from the model, a number of knot points of a representative CGO waveform may be obtained for any lung volume and the knot points may be used to reconstruct the CGO waveform of desired sample length using for example spline interpolation. The CGO waveforms in the bins may also be parametrized by other methods than spline fitting.

At stage 16, the obtained parametric CGO waveform model is used to generate a CGO waveform for each CGO encountered in the Z signal. The value of the model parameter, for example, the relative lung volume, is defined from the $\hat{Z}r$ signal at the particular time point or interval and the model is utilized to obtain a waveform corresponding to that parameter value. The generated CGO segments may have same or different length as the CGOs found in the Z signal.

At stage 17, the CGO waveforms generated by the parametric model are subtracted at corresponding locations from the Z signal in order to suppress the Zc signal and obtain a signal close to the pure Zr signal.

Figure 2:
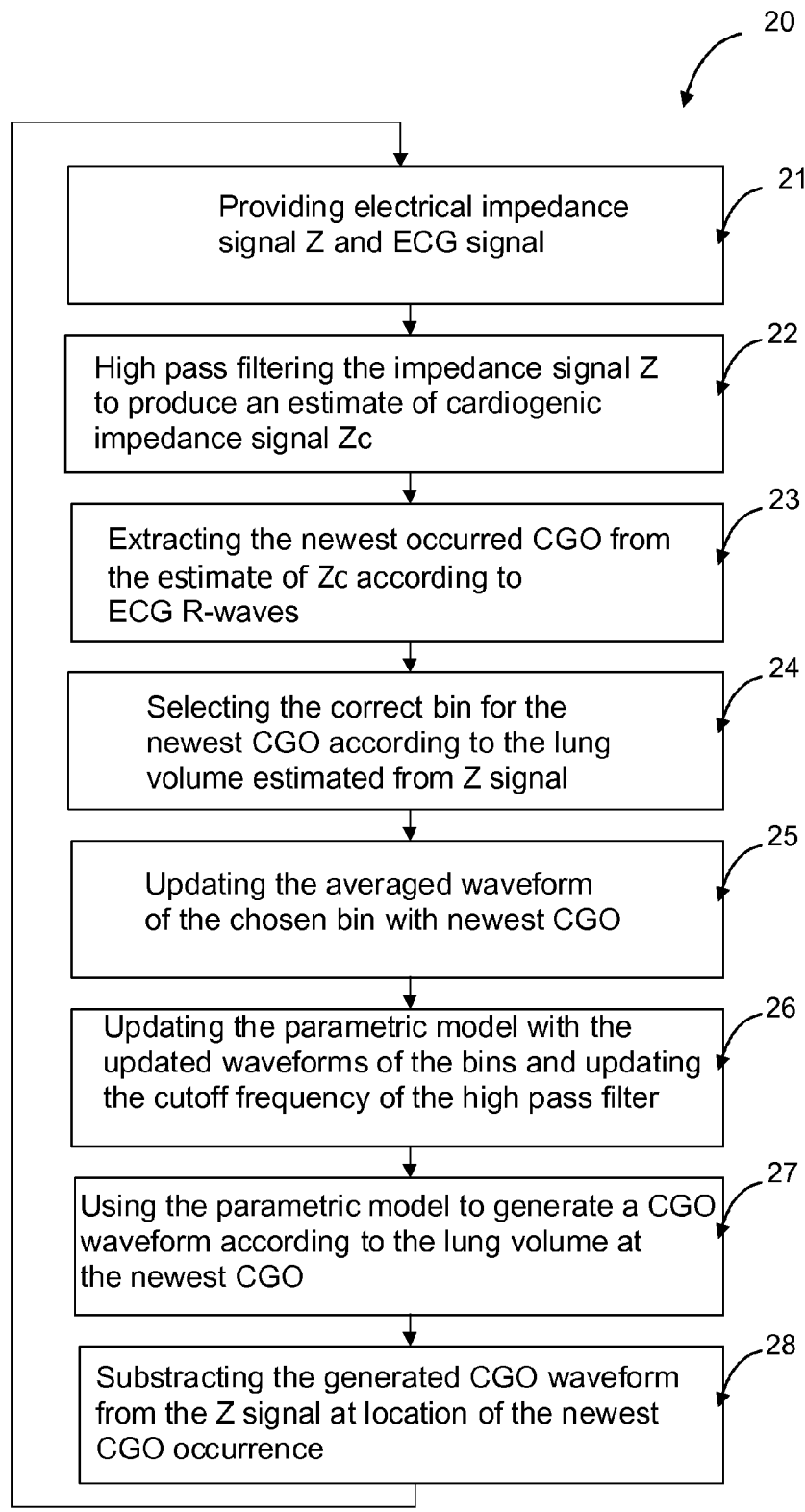
FIG. 2 shows a flowchart illustrating the steps employed in cancelling a cardiogenic impedance signal Zc from the impedance signal Z without altering the respiratory part Zr of the impedance signal Z, while updating the parametric model of the cardiogenic oscillation recursively over time, according to one embodiment of the present invention.

FIG. 2 shows a flowchart illustrating the steps of a method 20 for cancelling Zc, that is a cardiogenic part of a transthoracic electrical impedance signal Z, from the transthoracic electrical impedance signal Z without altering the respiratory part Zr of the transthoracic electrical impedance signal Z by forming a recursively adaptive parametric model of the cardiogenic oscillation, according to one embodiment of the present invention. This method 20 is suitable to be used especially for longer measurement periods, for example, in ambulatory 24-recordings, because the CGO waveform may change due postural and physiological changes. The method 20 is also suitable to be used, for example, during the measurement of a transthoracic electrical impedance signal Z for updating the parametric cardiogenic oscillation model from oscillation to oscillation as a real-time processing. The method 20 proceeds from the beginning of the measurement signals towards the end of the signals in time by processing Z signal segments defined in time by two consecutive ECG signal R-waves. The trigger signal may also be any other signal than ECG, like plethysmographic or pressure signal, that can be used to determine heart contraction timings or the segments can even be defined without any external trigger signal finding the contraction timings from the impedance signal itself.

At stage 21, the impedance signal Z and ECG are provided for a signal processing apparatus. The apparatus may be, for example, a special equipment for measuring and analyzing impedance data, a mobile terminal, a laptop computer, personal computer (PC) or any other data processing device that may comprise means for receiving or recording impedance and electrocardiogram (ECG) signals, means for signal processing and a memory. The memory may be any means for storing, for example, an internal memory of the apparatus. The Z and ECG signals maybe acquired from separate devices or from the same device using separate electrodes or the same electrodes for both.

At stage 22, an estimate of Zc, that is $\hat{Z}c$, may be obtained by high pass filtering the original impedance signal Z with a high pass filter with a predetermined cut-off frequency when this method 20 is performed first time for signal Z of the stage 21 or with a high pass filter with an updated cut-off frequency when this method 20 is performed two or more times for signal Z of the stage 21. Additionally, an estimate of Zr, that is $\hat{Z}r$, is produced as $\hat{Z}r = Z - \hat{Z}c$.

At stage 23, a single cardiogenic oscillation (CGO) as a segment of $\hat{Z}c$ between newly occurring and the previous ECG R-wave is extracted. The beginning and the end of the CGO signal are made zero values, in case they are not already zero. To make the beginning of the CGO signal zero, the value of the first sample may be subtracted from all samples of the CGO. For the end, a line between the first and the last sample may be subtracted from all samples of the CGO, or the end of the CGO sample may be convoluted with a decaying sample train ranging between 1 and 0. The amount of samples may be fixed by re-sampling the segment of $\hat{Z}c$ into a chosen amount of samples.

At stage 24, the lung volume at which the new CGO occurred is defined. The lung volume can be defined as a relative instantaneous volume of the particular respiratory cycle (0-100%) during which the CGO occurred or as related to some defined baseline volume. The volume may be obtained from the thoracic impedance signal Z, thus external volume measurements are not needed. The point in time at which the lung volume is defined may be the beginning, the end or any other point of CGO segment. It is also possible to define the lung volume as an average of lung volume values during the CGO segment. In addition, a bin to which the new CGO may be classified according to the defined lung volume is selected. The bins may also represent time phases of respiratory cycles instead of lung volumes or some other signal showing consistent modulation of the CGO waveform. The amount of bins should be more than 1, for example 4.

At stage 25, an ensemble average of a particular bin with the new CGO signal is updated. The existing CGO average signal is modified with the new CGO signal sample-by-sample using a weight factor i.e. a learning factor to define how strongly the average is affected by the new CGO signal i.e. how fast the algorithm adapts to changes. This results in a recursive adaptive CGO waveform estimate that bears information from the all previous CGO waves, but exhibits a progressive decay of the older CGOs. The weight factor is adapted according to any combination of the following factors: residual between the new CGO waveform and the average CGO waveform, ratio of the heart rate to the respiratory rate, change in posture or possible motion artefacts detected from an integrated accelerometer or some other source i.e. from a sphygmomanometer, or any other measurement that gives reason to suspect a fundamental change in the CGO waveform or reason to suspect that the observed CGO waveform change is not real i.e. artefacts.

At stage 26, the parametric model of the CGO is updated. The updated averaged representative CGO waveforms are used to construct and update a parametric model for the CGO waveform. The model outputs a representative CGO waveform for any particular value of the parameter that was used to divide the CGOs into bins, for example the relative lung volume obtained from $\hat{Z}r$. This model may be achieved, for example, by fitting a spline to each of the averaged CGO waveforms, obtaining a number of knot points in the waveform (disclosed in FIG. 5). Each of these knot points may then be assigned a piece-wise continuous function or any other function that takes the bin parameter as argument, for example, the relative lung volume, i.e. parametrizing the waveform. Thus, from the model, a number of knot points of a representative CGO waveform may be obtained for any lung volume and the knot points may be used to reconstruct the CGO waveform of desired sample length using for example spline interpolation. The CGO waveforms in the bins may also be parametrized by other methods than spline fitting. In addition, the cut-off frequency of the high pass filter that produces the $\hat{Z}c$ signal from the Z signal is updated. The cut-off frequency should be low enough to accommodate all spectral components of the cardiac impedance signal Zc but not unnecessarily low in order to exclude most of the respiratory part of the impedance signal Zr. The cut-off frequency may be obtained from a recursively adaptive heart rate frequency (HR) value multiplied with a factor below 1, for example 0.6*HR. Step of the stage 26, may be executed at any point of the method 20. The high-pass filter may have a previous updated cut-off frequency or the cut-off frequency may be predetermined cut-off frequency that is set for the filter before starting the method for decomposition of an additive signal consisting of oscillatory waveforms and a modulating signal.

At stage 27, a CGO waveform estimate according to the instantaneous lung volume is generated. The sparse representation of the CGO waveform is produced from the parametric model using the instantaneous lung volume at the moment as the input. The sparse representation is then expanded into a signal segment of necessary length at the particular CGO by spline interpolation or by some other similar method.

At stage 28, the CGO waveform estimate is subtracted from the impedance signal Z. This will efficiently cancel the cardiogenic impedance signal Zc without altering the respiratory part Zr of the signal Z. After, the step of stage 28, it is possible to get back to stage 21 again to perform the method 20 again for every CGOs.

Steps of stages 21-26 focus on updating the parametric cardiogenic oscillation model and they may be executed in different order. They may also be executed after steps of stages 27 and 28 relating to removing the cardiogenic oscillations from the Z signal.

Figure 3:
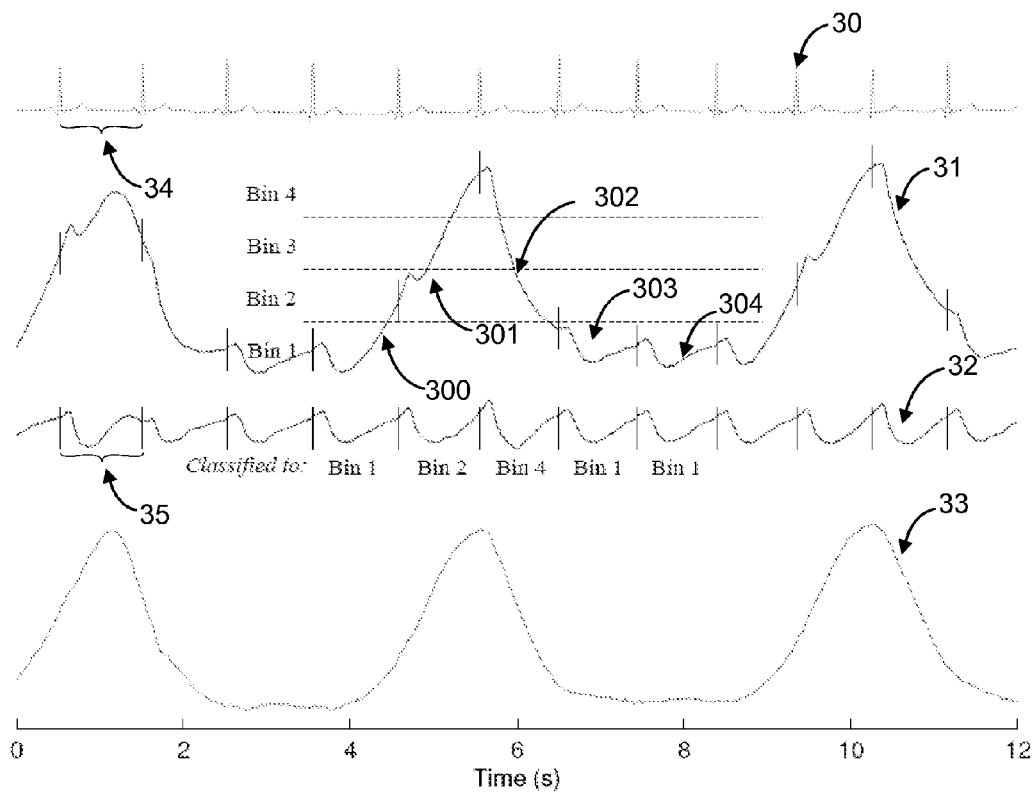
FIG. 3 shows an exemplified signals relating to a method, according to one embodiment of the present invention.
Figure 4:
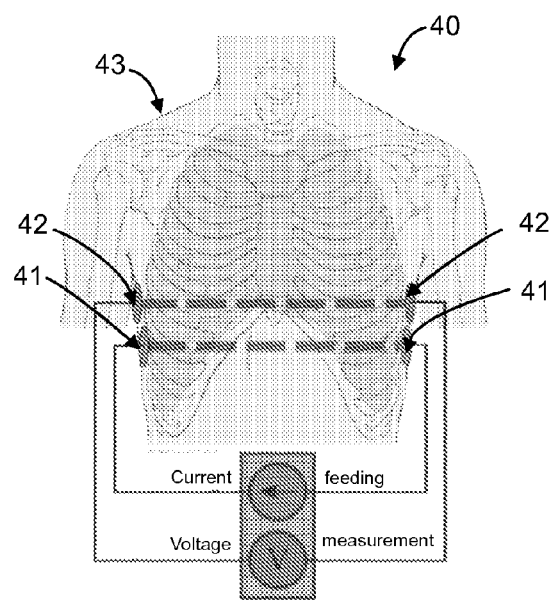
FIG. 4 shows an example of one possible electrode configuration according to an embodiment of the present invention.

FIG. 3 discloses exemplified signals 30, 31, 32, and 33 of a 12 second part of a longer impedance pneumography and electrocardiogram (ECG) recordings recorded from a subject during restful tidal breathing. These signals are either results of impedance pneumography and ECG recordings or signals that have been obtained by filtering the result signals of impedance pneumography and ECG recordings. The ECG signal 30 and a thoracic impedance signal Z 31 may be recorded simultaneously by using same electrodes. Possible electrodes may be, for example, commercial gel-paste Ag/AgCl electrodes designed for clinical ECG measurement, textile electrodes or any other electrodes suitable for recording impedance pneumography and ECG signals. One possible electrode configuration is illustrated in FIG. 4. A region 34 indicates an ECG wave, RR interval. Signal 32 is an estimate of the Zc-signal obtained from Z with a high pass filter. Vertical lines on the Zc-signal denote beginnings of individual cardiogenic oscillations, CGOs, and a region 35 between adjacent vertical lines indicates a single waveform of a cardiogenic oscillation.

The CGOs are classified to bins 1-4 according to the instantaneous lung volume and the beginning of the oscillation is used as the time of instant lung volume determination. For example, the CGO 300 is classified to Bin 1, the CGO 301 is classified to Bin 2, the CGO 302 is classified to Bin 4 and the CGOs 303 and 304 are classified to Bin4 as can be seen from the FIG. 3. However, it is also possible to utilize other binning variables like the phase of respiratory cycle instead of the relative lung volume. In addition, the time at which the value of the binning variable is determined could also be some other time of CGO than beginning, for example a center of CGO, or even an average of lung volume over the duration of the CGO.

A CGO waveform estimate may be generated according to the instantaneous lung volume. When the CGO waveform estimate is subtracted from the impedance signal Z, the cardiogenic impedance signal Zc is cancelled without altering the respiratory part of the impedance signal Zr. This result signal Zr, a filtered Z signal, is illustrated as a signal 33.

The impedance pneumography (IP), i.e. the bioimpedance, and ECG may be measured by using at least two electrodes. One possible electrode configuration 40 according to an embodiment is disclosed in FIG. 4, wherein a four electrode, tetrapolar, measurement setup is disclosed. This kind of measurement setup may decrease measurement errors caused by electrode skin interface. In this setup two electrodes 41 are used to feed a small alternation current, excitation current, into underneath tissue of a subject 43. Voltage generated by the current is measured by two other electrodes 42 on the other side of the subject 43. Impedance, Z, may be formed as a ratio between measured voltage, Umeasured, and fed current, Iexcitation:

$$Z = U_{measured} / I_{excitation}$$

Both used control signals, the ECG and the lung volume, are readily available in the IP measurement; the ECG signal can be measured from the same leads as IP and the lung volume information is intrinsically available in the IP signal. Thus, IP signal and ECG may be measured and recorded by using at least two electrodes, by same or separate electrodes or by any measurement configuration if the recorded signal is adequate for detection. In addition, the at least two electrodes can be located on any place of a subject according to what is to be measured.

Figure 5:
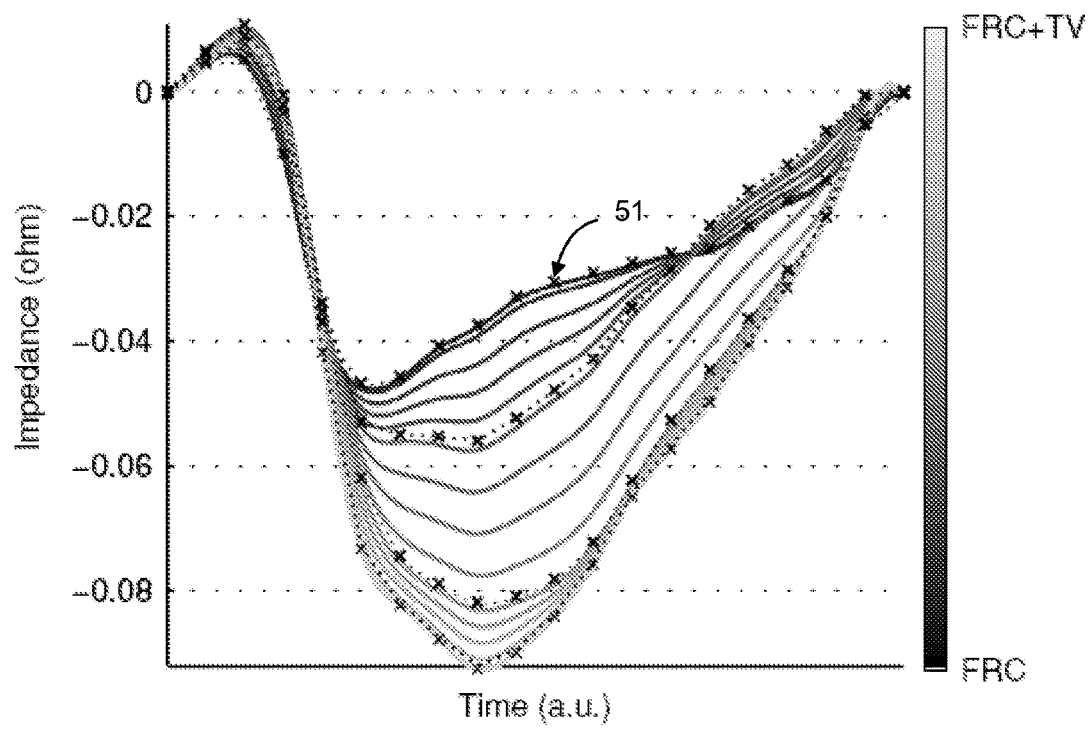
FIG. 5 shows an example of a change in cardiogenic oscillation waveform with lung volume change during tidal breathing.

Typical change in cardiogenic oscillation waveform with lung volume change during tidal breathing from functional residual volume (FRC) to FRC+tidal volume (TV) is disclosed in FIG. 5. The shape of the individual oscillations is modulated by the lung volume. An oscillation occurring at the beginning of expiration has a different waveform morphology than an oscillation occurring at the end of expiration. Thus, it should be noted, that in addition to different amplitudes, the oscillations may also have different shapes. The x 51 marks denote the 20 knot points of each of the four volume bins 1-4. The CGO waveforms are produced with cubic spline interpolation using the knot points adjusted to different lung volumes. As the FIG. 5 illustrates the CGO waveform shows an increase in amplitude with increasing lung volume, but the waveform change is not only a simple amplitude modulation. Thus, the modulation scheme may remain consistent if the physiological state and the posture of the subject remain constant.

Figure 6:
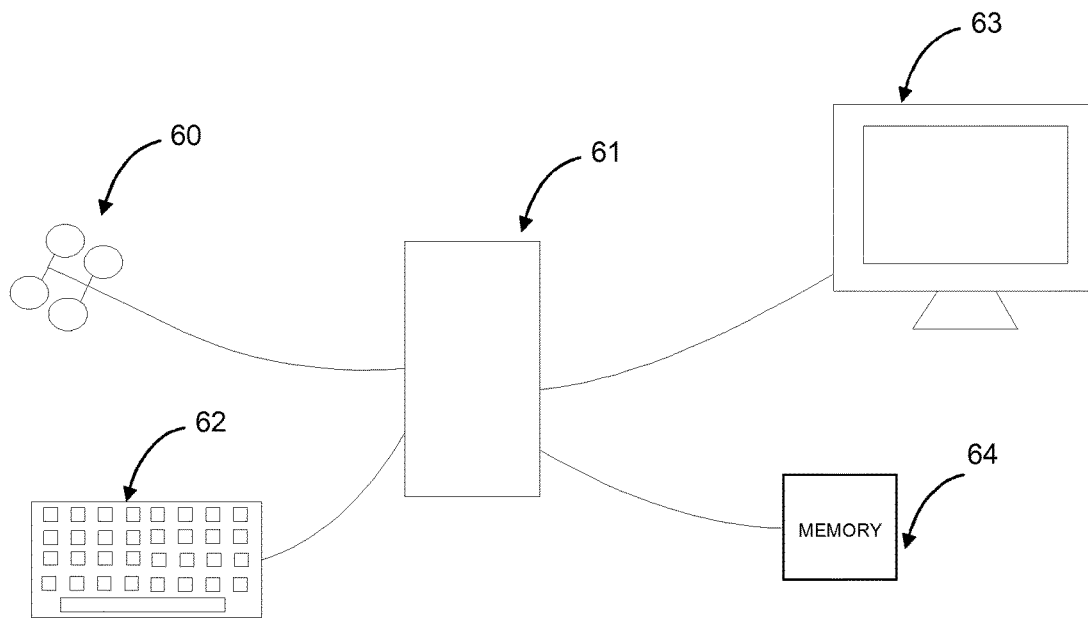
FIG. 6 shows a flow chart illustrating the steps of a method, according to one embodiment of the present invention.
Figure 7:
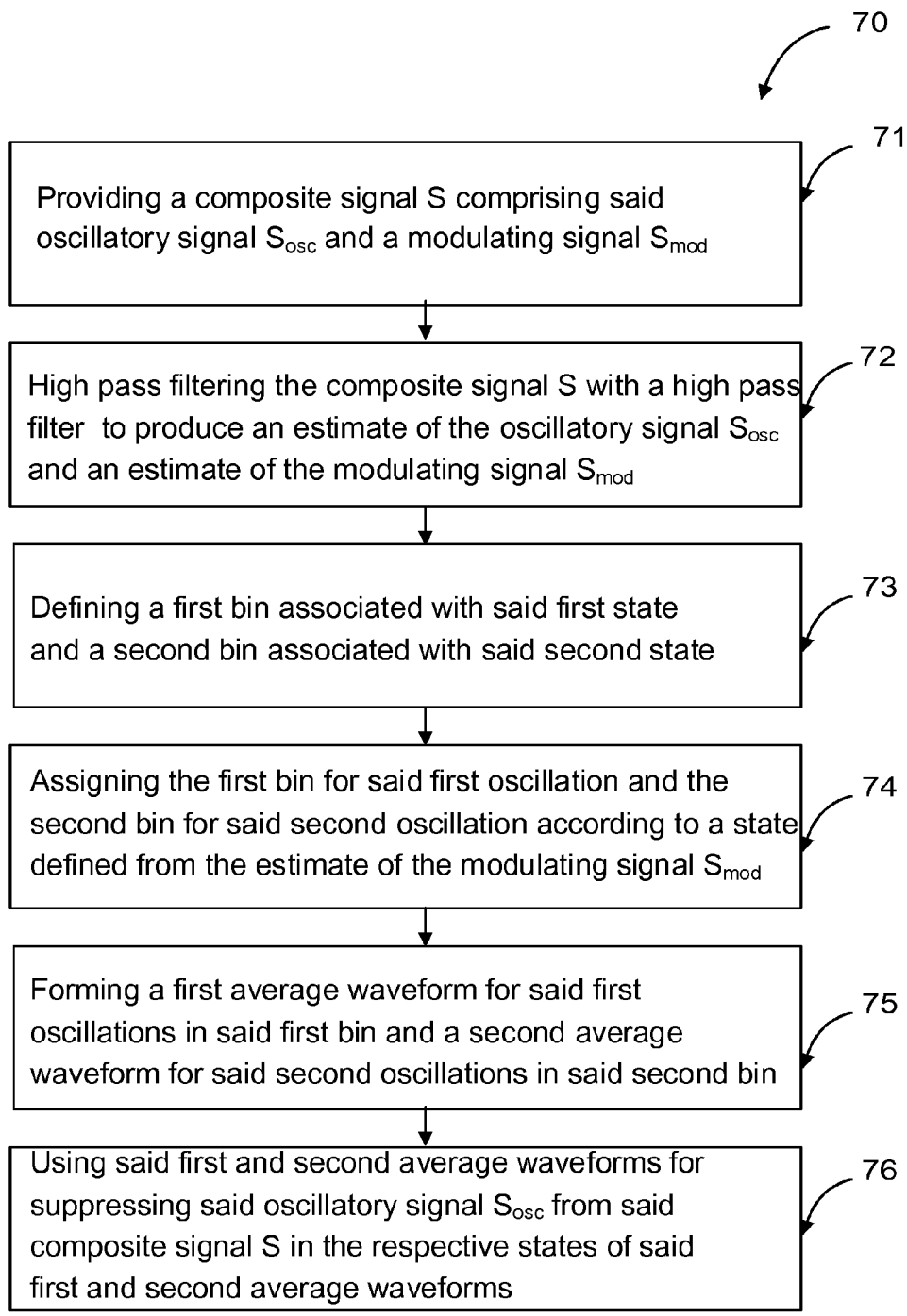
FIG. 7 is an example of a system for suppressing the cardiogenic oscillations in the impedance pneumography signal according to the present invention.

FIG. 6 illustrates a possible embodiment of the present invention. Electrodes 60, acting as a measuring unit, records transthoracic electrical impedance signal Z and ECG signal. These signals are fed to an apparatus 61 to be processed. The apparatus 61 is a processing unit comprising a processor and a computer program product stored on a storage medium comprising a computer program code. The apparatus 61 processes the signals Z and ECG according to the method of present invitation. The method used in apparatus 61 can be activated for example from the keyboard 62. The visual display unit 63 may show the graphical information of the recorded signals and/or result signals after suppression of the cardiogenic oscillations. Memory block 64 presents a recording feature for storing recorded signals and result signals wherefrom the cardiogenic oscillations are suppressed for possible later use and/or study. The memory block 64 may be an internal memory of the apparatus 61 or an external memory, FIG. 7 shows a flow chart illustrating the steps of a method 70 for suppressing an oscillatory signal Sosc, according to one embodiment of the present invention. At stage 71, a composite signal S comprising said oscillatory signal Sosc and a modulating signal Smod is provided.

At stage 72, the composite signal S is high pass filtered with a high pass filter to produce an estimate of the oscillatory signal Ŝosc and an estimate of the modulating signal Ŝmod, wherein the estimate of the oscillatory signal Ŝosc comprises first oscillations during a first state of the modulating signal Smod and second oscillations during a second state of the modulating signal Smod.

At stage 73, a first bin associated with said first state and a second bin associated with said second state are defined.

At stage 74, the first bin for said first oscillation according to a state defined from the estimate of the modulating signal Ŝmod and the second bin for said second oscillation according to a state defined from the estimate of the modulating signal Ŝmod are assigned. The state may be, for example, a phase or a value of a signal.

At stage 75, a first average waveform for said first oscillations in said first bin and a second average waveform for said second oscillations in said second bin are formed.

At stage 76, said first and second average waveforms are used for suppressing said oscillatory signal Sosc from said composite signal S in the respective states of said first and second average waveforms.

Figure 8:
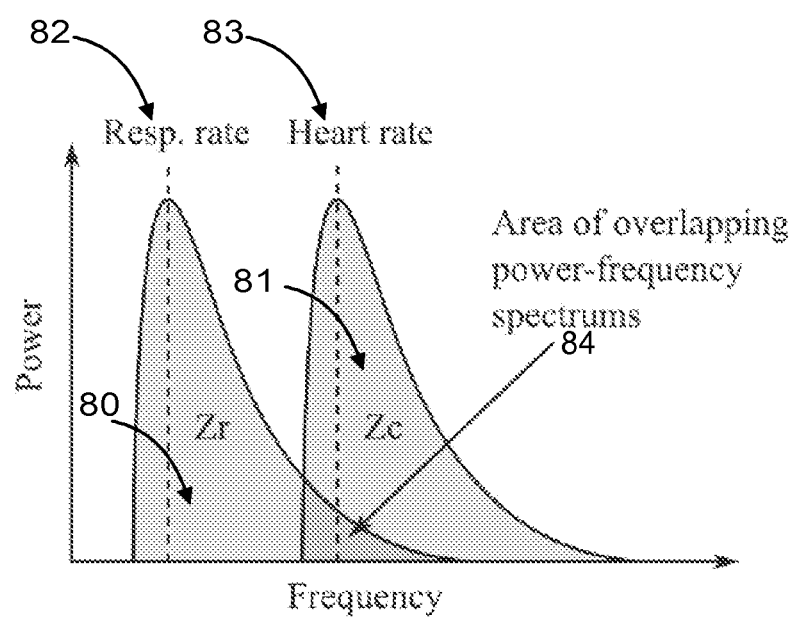
FIG. 8 shows an example of overlapping power-frequency spectrums.

FIG. 8 illustrates properties of the two signals, a respiratory signal Zr 80 and a cardiogenic signal Zc 81. The highest powers of the signals, 80 and 81, are in their fundamental frequencies which are respiratory rate 82 of the respiratory signal Zr 80 and heart rate 83 of the cardiogenic signal Zc 81. Most of the power is in frequencies above the fundamental frequencies 82, 83. The two signals, 80 and 81, partially overlap 84 in the frequency spectrum. Thus, a use of a linear filter, such as a low pass filter, would remove the cardiogenic signal Zc 81 efficiently, but it would also remove the high frequency components of the respiratory signal Zr 80. Thus, a linear filter is not suitable for removing the cardiogenic oscillations from respiratory signal Zr 80.

The various embodiments of the invention can be implemented with the help of computer program code that resides in a memory and causes the relevant apparatuses to carry out the invention.

It is obvious that the present invention is not limited solely to the above-presented embodiments, but it can be modified within the scope of the appended claims.

The invention claimed is:

1. A method for suppressing cardiogenic oscillations in a transthoracic electrical impedance signal, wherein a signal processing apparatus comprising at least one processor and at least one memory storing program instructions, when executed by the at least one processor, performs the steps of:
   providing a composite signal S being a transthoracic electrical impedance signal Z, comprising an oscillatory signal $S_{osc}$ being a cardiogenic part of the transthoracic electrical impedance signal Zc and a modulating signal $S_{mod}$ being a respiratory part of the transthoracic electrical impedance signal Zr, wherein the signals are time-series signals;
   high pass filtering the composite signal S with a high pass filter to produce an estimate of the oscillatory signal $\hat{S}_{osc}$ and subtracting the estimate of the oscillatory signal $\hat{S}_{osc}$ from the composite signal S to produce an estimate of the modulating signal $\hat{S}_{mod}$, wherein the estimate of the oscillatory signal $\hat{S}_{osc}$ comprises first oscillations during a first state of the modulating signal $S_{mod}$ and second oscillations during a second state of the modulating signal $S_{mod}$;
   defining a first bin associated with said first state and a second bin associated with said second state;
   defining the portions of the estimate of the modulating signal $\hat{S}_{mod}$ that correspond to said first state as the first state and that correspond to said second state as the second state;
   assigning the first bin for said first oscillations associated with the defined first state and the second bin for said second oscillations associated with the defined second state;
   forming a first average waveform for said first oscillations in said first bin and a second average waveform for said second oscillations in said second bin; and
   using said first and second average waveforms for suppressing said oscillatory signal $S_{osc}$ from said composite signal S in the respective states of said first and second average waveforms.

2. A method according to claim 1, further comprising generating a parametric model of the cardiogenic oscillation on the basis of the first and the second average waveforms.

3. A method according to claim 2, wherein the parametric model is generated by fitting a spline to the first and the second average waveforms for obtaining a number of knot points in the waveforms.

4. A method according to claim 2, further comprising forming a plurality of interpolated waveforms on the basis of the first and the second average waveforms.

5. A method according to claim 1, further comprising suppressing the cardiogenic oscillations in an impedance pneumography signal, wherein the cardiogenic oscillations and the impedance respiratory signal form a transthoracic impedance signal.

6. A method according to claim 1, wherein each of the first state and the second state is a phase of a signal or a value of a signal.

7. The method according to claim 6, wherein each of the first state and the second state comprises a lung volume of the modulating signal $S_{mod}$.

8. A system comprising a measuring unit and a processing unit comprising a memory and a computer program product stored on a memory comprising a computer program code configured to perform the method according to claim 1.

9. An apparatus comprising a memory and a computer program product stored on a memory comprising a computer program code configured to perform the method according to claim 1.

10. A computer program product stored on a non-transitory, computer-readable storage medium comprising a computer program code configured to, with at least one processor, cause an apparatus to perform the method according to claim 1.

11. A signal processing apparatus for suppressing cardiogenic oscillations in a transthoracic electrical impedance signal, comprising at least one processor, and at least one memory storing program instructions that, when executed by the at least one processor, causes the apparatus to:
   provide a composite signal S being a transthoracic electrical impedance signal Z, comprising an oscillatory signal $S_{osc}$ being a cardiogenic part of the transthoracic electrical impedance signal Zc and a modulating signal $S_{mod}$ being a respiratory part of the transthoracic electrical impedance signal Zr, wherein the signals are time-series signals;
   high pass filter the composite signal S with a high pass filter to produce an estimate of the oscillatory signal $\hat{S}_{osc}$ and to subtract the estimate of the oscillatory signal $\hat{S}_{osc}$ from the composite signal S to produce an estimate of the modulating signal $\hat{S}_{mod}$, wherein the estimate of the oscillatory signal $\hat{S}_{osc}$ comprises first oscillations during a first state of the modulating signal $S_{mod}$ and second oscillations during a second state of the modulating signal $S_{mod}$;
   define a first bin associated with said first state and a second bin associated with said second state;
   define the portions of the estimate of the modulating signal $\hat{S}_{mod}$ that correspond to said first state as the first state and that correspond to said second state as the second state;
   assign the first bin for said first oscillations associated with the defined first according to a state and the second bin for said second oscillations associated with the defined second state;

forming a first average waveform for said first oscillations in said first bin and a second average waveform for said second oscillations in said second bin; and use said first and second average waveforms for suppressing said oscillatory signal $S_{osc}$ from said composite signal S in the respective states of said first and second average waveforms.

12. An apparatus according to claim 11, wherein the processor causes the apparatus to generate a parametric model of the cardiogenic oscillation on the basis of the first and the second average waveforms.

13. An apparatus according to claim 12, wherein the processor causes the apparatus to generate the parametric model by fitting a spline to the first and the second average waveforms for obtaining a number of knot points in the wave-forms.

14. An apparatus according to claim 13, wherein the processor causes the apparatus to form a plurality of interpolated waveforms on the basis of the first and the second average waveforms.

15. An apparatus according to claim 11, wherein the processor causes the apparatus to suppress the cardiogenic oscillations in an impedance pneumography signal, wherein the cardio-genie oscillations and the impedance respiratory signal form a transthoracic impedance signal.

16. An apparatus according to claim 11, wherein each of the first state and the second state is a phase of a signal or a value of a signal.

17. An apparatus according to claim 16, wherein each of the first state and the second state comprises a lung volume of the modulating signal $S_{mod}$.

18. An apparatus according to claim 11, wherein the processing unit comprises:

a processor; and a computer program product stored on a storage medium.

* * * * *